United States Patent [19]

Young

[11] Patent Number: 5,451,206

[45] Date of Patent: Sep. 19, 1995

[54] TRIPLE LUMEN CATHETER

[75] Inventor: Pauline R. Young, Seattle, Wash.

[73] Assignee: Quinton Instrument Company, Bothell, Wash.

[21] Appl. No.: 309,365

[22] Filed: Sep. 20, 1994

Related U.S. Application Data

[63] Continuation-in-part of Ser. No. 101,517, Aug. 2, 1993, Pat. No. 5,348,536.

[51] Int. Cl.$^6$ .............................................. A61M 5/00
[52] U.S. Cl. .................................... 604/43; 604/280
[58] Field of Search ................. 604/43, 44, 45, 52–54, 604/164, 163, 264, 280–283

[56] References Cited

U.S. PATENT DOCUMENTS

| | | | |
|---|---|---|---|
| Re. 31,873 | 4/1985 | Howes | 128/674 |
| 3,314,430 | 4/1967 | Alley et al. . | |
| 3,359,974 | 12/1967 | Khalil . | |
| 3,394,705 | 7/1968 | Abramson . | |
| 3,437,088 | 4/1969 | Bielinski . | |
| 3,593,713 | 7/1971 | Bogoff et al. . | |
| 3,612,050 | 10/1971 | Sheridan . | |
| 3,726,281 | 4/1973 | Norton et al. . | |
| 3,746,003 | 7/1973 | Blake et al. . | |
| 3,828,767 | 8/1974 | Spiroff . | |
| 3,995,623 | 12/1976 | Blake et al. . | |
| 4,004,588 | 1/1977 | Alexander . | |
| 4,100,246 | 7/1978 | Frisch . | |
| 4,134,402 | 1/1979 | Mahurkar . | |
| 4,168,703 | 9/1979 | Kenigsberg . | |
| 4,180,068 | 12/1979 | Jacobsen et al. . | |
| 4,202,332 | 5/1980 | Tersteegen et al. . | |
| 4,257,416 | 3/1981 | Prager . | |
| 4,327,722 | 5/1982 | Groshong et al. . | |
| 4,385,631 | 5/1983 | Uthmann | 604/284 |
| 4,403,983 | 9/1983 | Edelman et al. | 604/43 |
| 4,406,656 | 9/1983 | Hattler et al. | 604/280 |
| 4,451,252 | 5/1984 | Martin | 604/43 |
| 4,484,585 | 11/1984 | Baier | 128/748 |
| 4,493,696 | 1/1985 | Uldall | 604/43 |
| 4,543,087 | 9/1985 | Sommercorn et al. | 604/43 |
| 4,559,046 | 12/1985 | Groshong et al. | 604/282 |
| 4,568,329 | 2/1986 | Mahurkar | 604/43 |
| 4,583,968 | 4/1986 | Mahurkar | 604/43 |
| 4,619,643 | 10/1986 | Bai | 604/43 |
| 4,626,240 | 12/1986 | Edelman et al. | 604/43 |
| 4,643,711 | 2/1987 | Bates | 604/4 |
| 4,682,978 | 7/1987 | Martin | 604/43 |
| 4,692,141 | 9/1987 | Mahurkar | 604/43 |
| 4,753,640 | 6/1988 | Nichols et al. | 604/247 |
| 4,772,268 | 9/1988 | Bates | 604/174 |
| 4,795,439 | 1/1989 | Guest | 604/43 |
| 4,822,345 | 4/1989 | Danforth | 604/282 |
| 4,894,057 | 1/1990 | Howes | 604/280 |
| 4,995,865 | 2/1991 | Gahara et al. | 604/43 |
| 5,057,073 | 10/1991 | Martin | 604/43 |
| 5,221,255 | 6/1993 | Mahurkar et al. | 604/43 |
| 5,221,256 | 6/1993 | Mahurkar | 604/43 |
| 5,378,230 | 1/1995 | Mahurkar | 604/43 |
| 5,395,316 | 3/1995 | Martin | 604/43 |

FOREIGN PATENT DOCUMENTS

| | | | |
|---|---|---|---|
| 1092927 | 1/1981 | Canada | 604/43 |
| 1150122 | 7/1983 | Canada . | |
| 0036642 | 9/1981 | European Pat. Off. | 604/43 |
| 0079719 | 5/1983 | European Pat. Off. . | |
| 0333308 | 9/1989 | European Pat. Off. . | |
| 1285953 | 7/1962 | France . | |
| 1508959 | 1/1968 | France . | |
| 2297640 | 8/1976 | France . | |
| 2530958 | 2/1984 | France . | |
| 2259865 | 6/1974 | Germany . | |
| 8404043 | 10/1984 | WIPO . | |

*Primary Examiner*—John D. Yasko
*Attorney, Agent, or Firm*—Andrew J. Beck; Montgomery W. Smith; Richard D. Allison

[57] ABSTRACT

An elongated catheter formed with multiple lumens from coextruded or other materials such that the inner surface of the extension members or body portion of the catheter may include a higher durometer than the outer surface of the extension members or body portion of the catheter to reduce septum deflection during normal use, and the likelihood of tearing or sticking of the extension members is reduced and the catheter includes a pair of generally cylindrical lumens and the catheter preferably includes a third lumen which is substantially smaller than the first two lumens and the cross sectional area of the lumens of the catheter are maximized with the septums of the catheter being oriented to maximize the flow of fluids through the catheter.

20 Claims, 4 Drawing Sheets

TRIPLE LUMEN CATHETER

RELATED APPLICATION

This is a continuation-in-part of application Ser. No. 08/101,517 filed on Aug. 2, 1993 now U.S. Pat. No. 5,348,536.

FIELD OF THE INVENTION

The present invention relates generally to a multiple lumen catheter for use in medical applications including hemodialysis catheters where fluids flow to and from a patient. This invention relates particularly to a catheter which has a lumen cross section which maximizes the flow characteristics of a multiple lumen catheter and which has sufficient softness and flexibility to remain inserted in patients for prolonged periods of treatment.

BACKGROUND OF THE INVENTION

Dual-lumen catheters have come into widespread use for extracorporeal blood purification procedures such as hemodialysis. Blood is withdrawn from the patient through one of the lumens of the catheter and supplied to a hemodialysis unit where the blood is dialyzed. The resulting dialyzed blood is then returned to the patient through the other lumen of the catheter. Examples of such catheters are shown in U.S. Pat. Nos. 4,134,402; 4,583,968; 4,568,329 and 4,692,141.

Many catheters for relatively long-term use are made of either polyurethane or silicone. Many polyurethane catheters are sufficiently rigid to be introduced into a patient's vein percutaneously without surgery. However, one of the difficulties with many polyurethane catheters is that they may be incompatible with the human body when left in the patient for relatively long periods of time such as a month or more.

The silicone catheters may be left in place for longer periods of time than many of the polyurethane catheters without allergic reactions or traumatic problems in most patients. However, one of the difficulties with silicone catheters is that the initial insertion of such catheters usually requires surgical intervention because the soft, pliable, elastic properties of the silicone which contribute to its compatibility with the human body are the same properties that make it difficult or impossible to insert the silicone catheter percutaneously into the vein of the patient.

Another problem encountered in using multiple lumen catheters for hemodialysis results from the flow of fluid through the lumens of the catheter. Typically one of the lumens of the catheter extends the full length of the catheter and is known as the venous or blood return lumen because the blood is returned to the body of the patient therethrough. The other lumen typically extends between the proximal end of the catheter and an opening in the sidewall of the catheter. This lumen is known as the arterial lumen because the blood flows through the lumen away from the body of the patient to the dialysis machine. During use of a hemodialysis catheter, a significant pressure differential is created across the septum due to the simultaneous flow of blood through the venous lumen under a positive pressure and through the arterial lumen under a negative pressure. With certain catheters, such as a silicone catheter, it is possible for the septum and the outside wall of the arterial lumen to collapse together, thereby closing the lumen and restricting the flow of blood therethrough. It is believed that the deflection of the septum is caused, at least in part, by the stretching of the septum or deformation of the lumens by the pressure gradient caused by the opposite flows of fluid through the lumens. This is particularly likely to occur in situations where the catheter is curved or bent.

A further problem which may be encountered when using single or multiple lumen catheters results from the repeated or long-term clamping of the extension members of the catheter. If the extension member is repeatedly clamped or clamped for a long period of time, the sidewalls of the extension member may stick together, and the catheter may become unusable. It is a common practice to use extension members formed of PVC or polyurethane material having a soft or lower durometer of about 72 to 85 A to provide the desired flexibility for the extension member. Although these materials have the desired flexibility, some of the softer materials may also have a tendency to become sticky on repeated or prolonged clamping and may remain partially or fully closed after repeated or prolonged clamping. Some catheters use silicone extension members which have sufficient flexibility for the intended use, and the sidewalls of the extension members do not have a tendency to stick together. The difficulty with the use of silicone materials for extensions is that silicone is extremely difficult to permanently bond to materials other than silicone, and the silicone extensions have a lower tear and tensile strength which may weaken the wall of the extension member after repeated clamping. Other commercially available catheters use a chemical coating on the interior surface of the extension to make the interior surface lubricous. One difficulty with the coated extension members relates to the difficulty of applying the lubricous coating to the extension member, and the coating may also wear off the interior surface of the extension member after repeated flushing of the catheter. Other catheters may use a urethane extension member which incorporates a waxy material therein which blooms to the surface of the extension member. Although the waxy material is believed to reduce the likelihood of the walls of the extension member sticking together, the waxy material may inhibit the adhesion or bonding of the extension member to the remaining components of the catheter.

A further difficulty arises with the use of single or dual lumen catheters when the clinician desires to obtain a blood sample for analysis and/or inject a medication into the blood vessel of a patient. With single or dual lumen catheters, the clinician must disconnect the catheter and/or flush the lumen before and after use. Similarly, when incompatible medications are administered to the patient, the clinician must carefully flush the lumen between medications.

In U.S. Pat. No. 5,221,255 granted to Mahurkar et al. a multiple-lumen catheter is disclosed which comprises an elongated cylindrical tube made of a soft elastic material and having an internal septum extending along the length thereof to form a pair of longitudinal lumens therebetween. A reinforcing member is disclosed as extending along the full length of at least one of the lumens for transmitting forces applied to the proximal end of the tube to the distal end of the tube. In a preferred embodiment of the Mahurkar application, the reinforcing member is embedded in the septum and is made of a material which is substantially stiffer than the material of the tube so that the catheter can be advanced against a resistance by the application of force to the proximal end of the catheter. The reinforcing member is described as also avoiding deformation and/or collapse of one or more of the lumens when a pressure gradient exists across the septum.

In a modified embodiment disclosed in the Mahurkar patent application, the cylindrical catheter has a pair of orthogonal flat internal dividers extending along the interior of the catheter for dividing the interior into three lumens extending along the length of the catheter. One of the lumens disclosed in this embodiment is described as having a D-shaped transverse cross section. The orthogonal dividers form a T-shaped septum which resists kinking of the catheter along the orthogonal transverse planes of the catheter.

As also disclosed in the Mahurkar patent application, the catheter is disclosed as being formed from a soft elastic material such as a silicone. The septum of the catheter is disclosed as being formed of a rigid material such as a nylon strip. Variations of the septum are also disclosed wherein the nylon strip has a T-shaped transverse cross section for a triple lumen catheter, a D-shaped transverse cross section or where the nylon strip is inserted into the catheter and then a thin layer of silicone is formed over the nylon strip to prevent the exposure of the fluids in the catheter to the nylon strip. As a further variation of the disclosed catheter, the dual lumen tube is described as being possibly coextruded with a continuous reinforcing strip of a material such as nylon in the septum.

One of the concerns which may be encountered by the approach disclosed in the Mahurkar patent application is that the nylon strip or other material may separate from the silicone portion of the catheter if the catheter is placed under a tensile load such as by stretching a portion of the catheter prior to insertion. The potential for separation is believed to be due primarily to the suggested use of materials which have significantly different elastic characteristics for the septum and catheter body.

The multiple-lumen catheter disclosed in the Mahurkar patent application also requires a number of additional manufacturing steps which may significantly increase the cost of manufacturing the disclosed catheter while similarly increasing the potential for quality control problems as compared to currently available catheters or the present invention.

Triple lumen catheters such as those described in U.S. Pat. Nos. 3,995,623 granted to Blake; 4,406,656 granted to Hattler et al.; 4,072,146 and 4,894,057 granted to Howes and 5,221,256 granted to Mahurkar, provide three independent dedicated lumens in a single catheter with lumen openings at different sites in the vein. Such catheters permit the simultaneous and continuous infusion and/or monitoring of the patient. As a result of the flexibility provided by these catheters, they are the catheters of choice in managing seriously ill patients. These triple lumen catheters are not optimal for the treatment of critically ill hemodialysis patients because of their inefficient flow geometry. The cross sectional area of these triple lumen catheters is not maximized and therefore the flow characteristics of these catheters is not optimized. In hemodialysis it is desirable to have a catheter which allows a bi-directional flow of approximately 250 ml per minute with a pressure gradient under 100 mm of mercury. Therefore, in order to understand the best way to maximize the geometry of the catheter it is important to understand Poiseuille's Law which relates to the velocity of the flow of a liquid through a constrained area such as a capillary tube or the lumen of a catheter. According to Poiseuille's Law, the velocity of the flow of a liquid though a lumen varies directly to the pressure of the liquid and the fourth power of the diameter of the lumen and inversely to the length of the lumen and the coefficient of viscosity. Therefore, the flow of a fluid through a catheter may be maximized by maximizing the area of the lumen while minimizing the surface area of length of the walls forming the lumen of the catheters. With hemodialysis catheters, this creates a conflict between the need to have two lumens which have the flow characteristics of a dual lumen catheter while providing a third lumen for the administration of medications and/or monitoring of the venous pressure of the patient. In U.S. Pat. No. 5,221,255 granted to Mahurkar, this desire to optimize the size of the first and second lumens is explicitly expressed. Despite this expressed desire, the Mahurkar patent discloses a triple lumen catheter which fails to optimize the cross sectional area of the lumens and which unnecessarily increases the length of the walls surrounding the respective lumens of the catheter. In one of the objects disclosed in the Mahurkar patent, the reason for this compromise in the flow characteristics is described as being necessary to provide a third lumen which may be used to contain a removable stylus to provide the catheter with sufficient column strength to allow for the insertion of the catheter over a flexible Seldinger guide wire without buckling or kinking. As a result of this expressed desire to accommodate a guide wire in the third lumen, the third lumen is shown and described as having a circular cross section which impinges on the cross sectional areas of the first and second lumens. As explained by Poiseuille's Law, this inefficient use of the diameter of the lumens results in a significantly reduced efficiency in all three lumens of the catheter.

Therefore, a need remains for a catheter which maximizes the diameter of the lumens of the catheter and which minimizes the length of the walls which form the lumens.

Similarly, a need remains for a catheter which has sufficient flexibility and softness to be used for prolonged periods of treatment while being able to be inserted nonsurgically and manufactured consistently and cost effectively.

SUMMARY OF THE INVENTION

It is an object of the present invention to provide an improved catheter having multiple lumens which maximize the cross sectional area of each of the lumens while minimizing the length of the walls which surround the lumen.

It is another object of the present invention to provide an improved catheter having one or more lumens therein which may be made of silicone or other relatively soft, elastic materials which are unlikely to be rejected by the body, and thus can be used for long-term applications, and yet has sufficient rigidity or column strength to be inserted into a patient without surgery.

It is yet another object of the present invention to provide increased stiffness across the septum of the catheter while not significantly altering the overall resiliency of the catheter.

It is a further object of the present invention to provide an improved catheter having an outer surface which may be made of silicone or similarly soft materials and an inner surface of different or more rigid materials and yet may be inserted into the patient in a conventional manner, guidewire and peel-apart sheath; i.e., without surgical intervention.

Further objects of the present invention will become apparent by reviewing the preferred forms of the present invention which are set forth in detail below.

In a preferred form of the present invention, the catheter includes a pair of single lumen extension members on the proximal end thereof and a preformed tip having a single lumen on the distal end thereof. The extension members are preferably formed by a coextrusion process so that the interior surface of the extension members are formed of a material which has a higher or harder durometer than the exterior surface of the extension members to allow the extension members to be clamped for prolonged periods of time without having the interior surface of the extension member sticking together.

The catheter of this embodiment preferably includes one or more septums therein, and the body portion of the catheter is preferably formed by a coextrusion process such that the septum, the lumen, or the septums and the interior surface of one or more of the lumens is formed of a somewhat rigid material having a higher or harder durometer than the exterior surface of the body portion of the catheter. The use of the coextruded harder material for the septum, the lumen or the septum and the coextruded interior surface of one or more of the lumens reduces the deflection of the septum while not significantly altering the overall resiliency of the catheter. The coextrusion process used in the present invention further ensures that the softer and harder durometer materials are integral with each other so that there is no likelihood of separation upon repeated or extreme flexing of the catheter.

In a further preferred form of the present invention, a triple lumen catheter is disclosed which is particularly useful as a hemodialysis catheter while providing a third lumen which has a diameter sufficient for the administration of medications and/or monitoring the venous pressure of a patient. As described more fully below, the cross sectional area of the third lumen is significantly smaller than the cross sectional areas of the first and second lumens so that the first and second lumens will provide the desired flow characteristics for a hemodialysis catheter. In this preferred form of the present invention, the shorter portions of the septum or the legs of the septum which form two of the walls of the third lumen extend linearly from the primary septum wall to maximize the cross sectional area of each of the lumens while minimizing the length of the walls necessary to form the respective lumens.

An advantage of the present invention is that the cross sectional area of the third lumen is maximized while the impact on the cross sectional area of the first and second lumens is minimized to form a catheter which is particularly useful with critically ill hemodialysis patients.

Another advantage of the present invention is that the coextruded extension members of the catheter retain the resilient characteristics of lower durometer materials such as the currently available PVC, urethane or polyurethane extension members while preventing the sticking of the sidewalls of the extension after repeated or prolonged clamping found with many of the currently available extension members.

Yet another advantage of the present invention is that the materials used herein may be permanently bonded or otherwise adhered to the remaining components of the catheter.

A further advantage of the present invention is that the likelihood of septum deflection or catheter kinking is decreased without increasing the catheter size or decreasing the flow rates through the lumens of the catheter.

A further advantage of the present invention is that the stiffness of the extensions and/or the body portion of the catheter may be varied according to the intended use of the catheter by increasing or decreasing the thickness or durometer of the inner or outer layers of the catheter either along their entire length or in selected areas.

DESCRIPTION OF THE PREFERRED EMBODIMENTS

Figure 1:
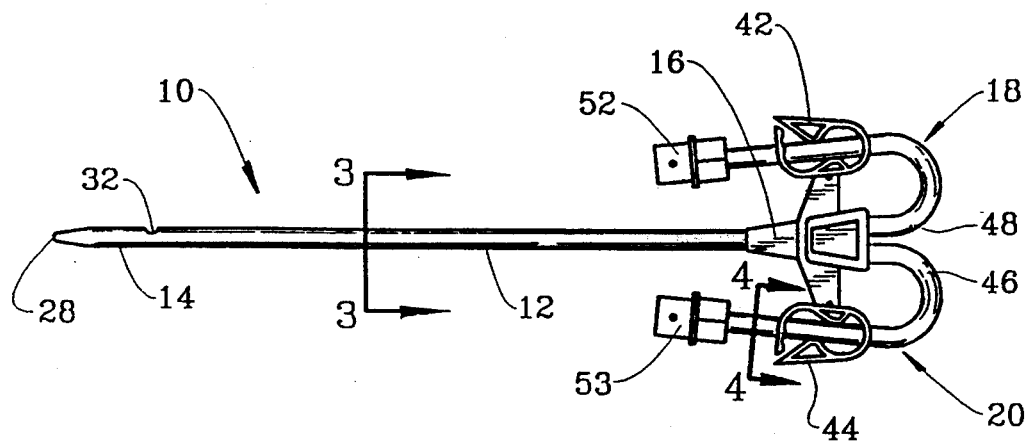
FIG. 1 is an elevated side view of a dual lumen catheter constructed in accordance with the present invention.

As shown in the drawings, the presently preferred form of the catheter assembly 10 of the present invention is generally similar to the dual lumen hemodialysis catheter shown in U.S. Pat. No. 4,583,968 granted to Mahurkar on Apr. 22, 1986. The preferred catheter assembly 10 generally includes an elongate and slightly oval shaped body portion 12 having a tip member 14 on the distal end thereof and a Y-shaped connector hub 16 on the proximal end thereof. As shown in FIG. 1, the proximal end of the Y-connector includes extension members 18 and 20 thereon. As used herein, the term "proximal" is intended to refer to the end or portion of a member which is normally oriented or positioned away from the patient while the term "distal" refers to the end or portion of a member in use which is nearest to the patient. Although the preferred form of the present invention is described herein with respect to multiple lumen catheters, it is intended that the present invention may also be used with nearly any single lumen catheter including angiographic or various diagnostic catheters.

Figure 2:
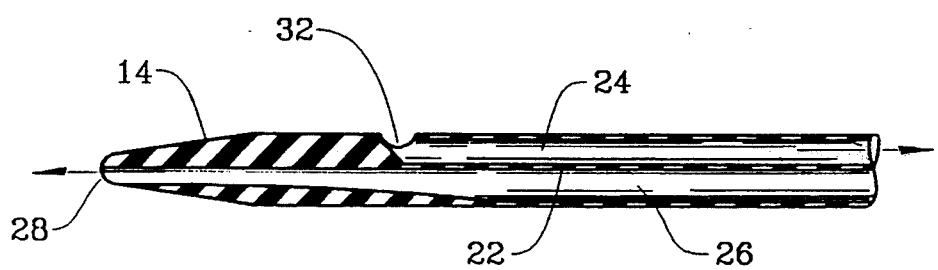
FIG. 2 is an enlarged cross-sectional view of the distal end portion of the catheter shown in FIG. 1.
Figure 3:
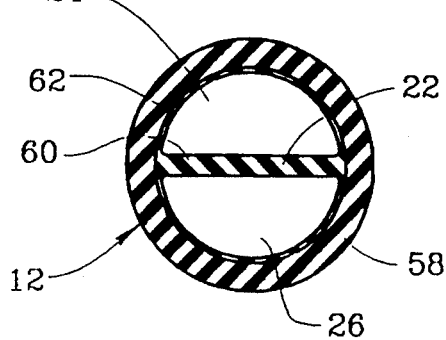
FIG. 3 is an enlarged cross-sectional view taken generally along lines 3—3 of FIG. 1 showing the cross section of the multiple-lumen catheter of FIG. 1.
Figure 5:
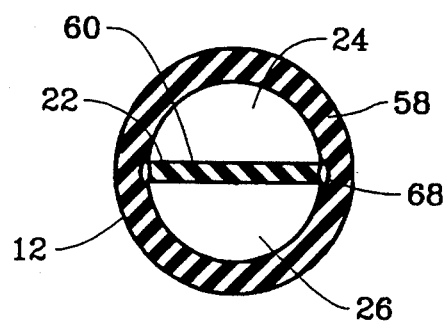
FIG. 5 is an enlarged cross-sectional view of an alternate embodiment of the present invention showing the septum and lumen of the alternate catheter embodiment taken generally in the same area of the alternate embodiment as lines 3—3 of FIG. 1.

The body portion 12 of the catheter assembly 10 is hollow except for a generally flat, longitudinal septum 22 which preferably divides the interior of the hollow cylinder into two parallel lumens 24 and 26, each preferably having a generally D-shaped cross section (FIGS. 3 and 5). As illustrated by the arrows in FIG. 2, the lumen 24 is the blood-intake or arterial lumen, and the lumen 26 is the blood-return or venous lumen.

At the distal end of the catheter assembly 10, the exterior surface of the body portion 12 merges into the smoothly tapered conical tip member 14. On the inside of the body portion 12, the blood-return lumen 26 extends longitudinally all the way through the tip member 14, bending slightly as it passes through the tip member 14 so that it opens at distal opening 28 near the center of the distal end of the tip member as can be seen in FIG. 2. Within the tip member 14 the cross-sectional shape of the lumen 26 gradually changes from D-shaped at the proximal end of the tip member 14 to circular at the distal end of the tip member 14 at the distal opening 28.

In addition to the distal opening 28 at the distal end of the blood-return lumen 26, one or more apertures may be formed in the sidewall of the return lumen. These apertures would be spaced longitudinally away from the distal opening 28 toward the proximal end of the catheter assembly 10 to ensure the flow of blood through the return lumen 26 even in situations where the distal opening 28 might become wholly or partially blocked.

In order to provide a longitudinal spacing between the distal openings of the two lumens 24 and 26, the blood-intake lumen 24 is terminated at side opening 32 in the sidewall of the catheter. Additional openings may be spaced longitudinally from the side opening 32 to permit blood to enter the lumen 24 freely without excessive vacuum in the event of a blockage of the side opening 32 against the wall of the vein into which the catheter assembly 10 is inserted.

At the proximal end of the catheter 10, the two D-shaped lumens 24 and 26 connect to a Y-shaped connector hub 16 which forms two internal passageways communicating with the proximal ends of the catheter lumens 24 and 26. The passageways of the connector hub 16 diverge from each other and assume a circular cross section as they extend toward the proximal end of the connector hub 16. The passageways may also increase in cross-sectional area as they extend toward the proximal end of the connector hub 16. The connector hub 16 is preferably molded in place on the end of the catheter, using core pins to form the hub passageways. Alternatively, the walls of the catheter lumens 24 and 26 may be expanded at the proximal end of the catheter to fit over the corresponding portions of a preformed connector hub 16 with the inside walls of the catheter lumens 24 and 26 being bonded to the mating walls of the connector hub 16.

To facilitate connection of the connector hub 16 to the conventional tubes leading to a dialysis unit, and also to accommodate a pair of clamps 42 and 44 for opening and closing the blood-intake and return lumens 24 and 26, the connector hub 16 is fixedly attached to a pair of tubular extension members 18 and 20 as shown in FIG. 1. These extension members 18 and 20 are relatively soft and flexible so that they can be manipulated and also easily closed by the pressure of the clamps 42 and 44. As shown in FIG. 1, the extension members 18 and 20 of the presently preferred embodiment are preferably precurved or bent to facilitate the positioning of the extension members 18 and 20 along the body of the patient when the catheter assembly 10 is inserted therein. The clamps 42 and 44 serve as on-off valves for controlling the flow of blood between the catheter assembly 10 and the dialysis unit. A pair of luer connectors 52 and 53 are used to couple the proximal ends of the extension members 18 and 20 to the flexible tubes (not shown) leading to the extracorporeal or dialysis blood treatment unit.

Figure 4:
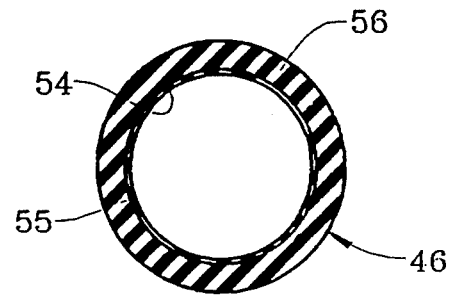
FIG. 4 is an enlarged cross-sectional view taken generally along lines 4—4 of FIG. 1 showing the cross section of an extension member of the present invention.

In one form of the present invention, the extension members 18 and 20 may be coextruded to the desirable features of the preferably non-sticky materials such as a silicone or a harder plastic material while maintaining the resiliency, increased tensile strength and tear resistance found in many of the currently available PVC, urethane or polyurethane materials. As shown in FIG. 4, the coextrusion preferably forms a thin inner layer 54 of a material which is harder than the thicker and softer outer layer 56. In a generally preferred form of the present invention, the outer layer 56 is preferably about ten times thicker than the inner layer 54 although it is believed that these proportions may be varied according to the desired characteristics of the curved extension members 46 and 48. One preferred combination of coextruded materials uses a soft outer layer 56 having a lower durometer in the range of between about 50 A to about 93 A and a harder inner layer 54 having a higher durometer in the range of between about 90 A to about 75 D. In a more preferred form of the present embodiment the outer layer 56 of the curved extension members 46 and 48 is preferably formed of a material having a durometer of about 80 A which is about 0.027 inches thick and an inner layer 54 which is formed of a material having a durometer of about 90 A and a thickness of about 0.003 inches or about one-ninth of the thickness of the outer layer 56.

Although the thickness of the inner and outer layers 54 and 56 may be varied according to the desired rigidity of the extension members 18 and 20; and it is believed that if straight extension members 64 and 66 (FIG. 9) are used, the thickness of the inner layer 54 may be reduced significantly to increase the flexibility of the extension members 64 and 66 while minimizing the stickiness or tearing of the extension member 64 or 66. Therefore, with the present embodiment, it is preferred that the inner layer 54 be as thin as possible so that the flexibility of the extension members 64 and 66 is similar to extension members which are formed of the softer outer material only.

The coextruded extension members 18 and 20 may also be more easily solvent, heat bonded or otherwise fixedly attached to the connector hub 16 or luer connectors 52 and 53 than currently available silicone extension members. Currently available connector hubs and luer connectors are commonly formed of a plastic material which is oftentimes difficult to securely attach to an extension member that may have a lubricous coating or waxy surface thereon. Additionally, although FIG. 4 shows the inner and outer layers 54 and 56 as being distinct layers of different materials, the time, temperature and/or other manufacturing variabilities of the coextrusion process may be adjusted to produce a thinner or thicker intermediate layer 55 which is formed by a combination of the coextruded materials. The existence of the intermediate layer 55 prevents the separation of the respective materials even if the extension members 18 and 20 are repeatedly bent or otherwise placed under a tensile load by the user.

In accordance with another presently preferred form of the present invention, the outer layer 58 of the body portion 12 of the catheter assembly 10 is preferably formed of a soft outer material which has a preferred durometer in the range of about 50 A to about 55 D. One such preferred material is pellethane 55 D manufactured by Dow Chemical of Midland, Mich., U.S.A., with approximately 15% barium sulfate and 1% titanium oxide therein. Other materials such as various urethanes or silicones may also be used to provide an outer layer 58 which is compatible with the relatively long-term implantation of the catheter assembly 10 in the tissue of the patient. For example, it is believed that a silicone material having a durometer generally in the range of about 50 A to 93 A may be acceptable. Another preferred material for the outer layer 58 is a pellethane material having a durometer of about 80 A with approximately 15% barium sulfate and 1% titanium oxide therein.

The inner layer 60 of the body portion 12 is preferably formed of a harder inner material which has the same or a higher modulus or durometer than the outer layer 58 to reduce the likelihood of septum deflection during use. The material of the inner layer 60 preferably has a durometer generally in the range of about 90 A to 75 D and, in a preferred form of the present invention, the inner layer 60 forms the septum 22 and a relatively thin surrounding layer around the intake and return lumens 24 and 26 as shown in FIG. 3. A more preferred material for the inner layer 60 has a durometer of about 55 D and is a pellethane material.

The preferred method of manufacturing the present invention involves the coextrusion of the materials used for the outer layer 58 and inner layer 60 of the body portion 12 of the catheter assembly 10 such that the two surfaces are formed and extruded at the same time and are integral with each other. This preferred method of coextrusion manufacture of the present invention is in contrast to the other method of coextrusion manufacture referred to in the above-identified Mahurkar et al. patent. The coextrusion method disclosed in the Mahurkar et al. patent involves a coextrusion process wherein an outer or inner layer is extruded over a preexisting inner or outer layer. The latter method of coextrusion may be subject to separation of the respective layers while the method of coextrusion used in the present invention forms an intermediate layer therebetween such that the respective layers are integral with each other. Additionally, the coextrusion of the present invention preferably reduces the likelihood of septum deflection while not significantly increasing the column strength of the catheter. This is in comparison to the method of coextrusion disclosed in the Mahurkar patent which is disclosed as increasing the column strength of the catheter.

As shown in FIG. 3, the outer diameter of a preferred form of the body portion 12 is preferably about 0.158 inches, and the width of the intake and return lumens 24 and 26 are preferably about 0.118 inches wide and about 0.050 inches high. The lower durometer or modulus material which is used to form the outer layer 58 of the body portion 12 is preferably about 0.015 inches thick. The material of the outer layer 58 surrounds the higher durometer material of the inner layer 60 which surrounds the intake and return lumens 24 and 26 of the present embodiment. The higher durometer or modulus material is preferably about 0.005 inches thick or about one-third of the thickness of the outer layer 58 around the intake and return lumens 24 and 26 and is formed integrally with the septum 22. The septum 22 is preferably about 0.012 inches thick in the present embodiment.

Although FIG. 3 shows the layers of higher and lower durometer materials as being substantially distinct layers, the coextrusion process provides a body portion 12 which includes an intermediate layer 62 having a mixture of the materials from each layer therein. The thickness of this intermediate layer 62 is variable according to the manufacturing process and the desired characteristics of the final product.

The width of the layer of higher durometer material which surrounds the intake and return lumens 24 and 26 may be adjusted according to the anticipated use of the catheter assembly 10 such that, if the use of the catheter assembly 10 is anticipated to include multiple or severe curves or bends of the body portion 12, it may be desirable to coextrude the materials so that the width of the higher durometer material is decreased in the typical area of the curve or bend of the catheter to increase the desired flexibility of the catheter in this area while maintaining the stiffness of the septum and/or catheter in the remainder of the catheter without significantly increasing the likelihood of septum deflection. For example, if an area of the catheter is typically subject to a severe curve or bend, it may be desirable to decrease the rigidity or hardness of the inner layer by decreasing the thickness of the inner layer, or by increasing the softness of the outer layer by increasing the relative thickness of the outer layer. Alternately, it may be desirable to increase the rigidity or hardness of a portion of the catheter in the area of a preformed curve to limit undesirable bending or deflection in the curved area or to form a precurved area in the desired portion of the catheter.

This may be accomplished by increasing the thickness of the inner layer in the desired area or by reducing the relative thickness of the outer layer.

As shown in FIG. 5 and described briefly above, a catheter assembly 10 in accordance with the present invention may include a body portion 12 wherein the septum 22 is formed of a higher durometer material, and the remainder of the body portion 12 is formed of a softer, lower durometer material. In this embodiment, an intermediate layer 68 is formed along the ends of the septum 22 in the sidewalls of the body portion 12 to ensure that the septum 22 is an integral part of the body portion 12. As shown, the innermost surface of the lumens 24 and 26 which are adjacent to the septum 22 are formed by the higher durometer material while the outermost surface of the lumens which are formed by the sidewalls of the catheter are formed by the lower durometer material. In the embodiment shown in FIG. 5, the body portion 12 preferably has sufficient stiffness across the septum such that the likelihood of septum 22 deflection is reduced during use of the catheter assembly 10 while having more sidewall flexibility and less column strength than the embodiment shown in FIGS. 1–4. As a further alternative to the embodiments described in FIGS. 1 ∝ 4 and 5, it is believed that a further variation of the present invention (not shown) may be formed wherein the septum 22 is formed of a higher durometer material, and the intermediate layer is formed to surround the lumens 24 and 26 so that the softer outer layer surrounds the intermediate layer which surrounds the lumens 24 and 26 and the harder septum 22.

Figure 6:
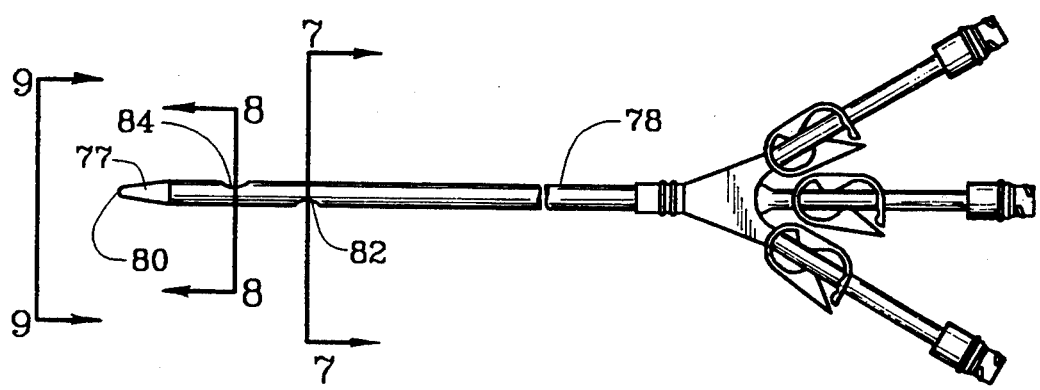
FIG. 6 is an elevated diagrammatic side view of a triple lumen catheter constructed in accordance with the present invention.
Figure 7:
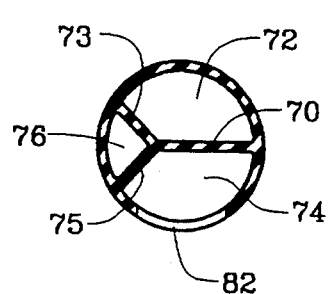
FIG. 7 is an enlarged cross-sectional view of the further alternate embodiment of the present invention of FIG. 6 showing the septum of a triple-lumen catheter constructed in accordance with the present invention taken generally along lines 7—7 of FIG. 6.

FIGS. 6–13 show further embodiments of the present invention wherein the catheter assembly is a triple lumen catheter, and FIGS. 8–12 have been added to amplify and further explain the invention shown in FIGS. 6 and 7. The major septum 70 of the embodiment shown in FIGS. 6–9 may be formed of a higher durometer material similar to the material described above with respect to the septum of the preferred embodiment of the present invention, and the intermediate layer 71 is preferably formed at the intersection of the ends of the septum 70 and the body portion 78 of the catheter. The septum 70 and the minor septums 73 and 75 of this embodiment separate the interior of the catheter assembly into three distinct lumens—72, 74 and 76.

The two primary lumens 72 and 74 preferably include the majority of the cross-sectional area of the catheter and preferably function as venous and arterial lumens when the catheter assembly is used for hemodialysis. The third lumen 76 is formed by or transversely oriented or slightly bent (FIGS. 7, 11, 12 or 13) minor septums, such as minor septums 73 and 75 (FIG. 7) which intersect the diametral end of the major septum 70 that is opposite the portion of the major septum 70 that intersects the body portion 78 such that each one of the ends of each of the major and minor septums, 70, 73 and 75, contact the sidewalls of the body portion 78 of the catheter at an angle greater than or equal to ninety degrees along the first and second lumens 72 and 74 to reduce the likelihood of a stagnant flow area at this intersection. The third lumen 76 allows the nurse or physician to inject medications through the catheter without concern about possible adverse reaction or contamination caused by injecting the medication through the primary lumens 72 or 74 of the catheter.

The location of the openings in this embodiment are best shown in FIG. 6. As with the prior embodiment, the venous or blood return lumen 72 extends through the catheter assembly to an opening 80 which is preferably located at the distal end of the catheter tip member 14. The arterial lumen 74 extends through the catheter assembly to an opening 82 located in the sidewall of the catheter assembly. The third lumen 76 extends through the catheter assembly to an opening 84 which is positioned between openings 80 and 82 and generally offset from opening 82. In the preferred form of the present invention, the distance between openings 80 and 82 is approximately twice as much as the distance between openings 80 and 84 so that when blood is drawn into opening 82, the medication injected into the vein through opening 84 will not be drawn into opening 82. In the embodiment shown in FIGS. 6 and 7, the opening 84 for the third lumen 76 is preferably located approximately 0.68 inches from opening 80 on the distal end of the catheter. The opening 82 for the arterial lumen 74 is preferably located approximately 1.3 inches from opening 80 on the distal end of the catheter.

It should be understood that the major septum 70 need not be perfectly flat, but could have a minor degree of curvature or other geometric configuration, it is preferred in this embodiment that the major septum 70 and the minor septums 73 and 75 be substantially flat to maximize the cross-sectional area of the respective lumens formed by the septums and the body portion 78, while minimizing the length of the septums which form the respective lumens to maximize the flow of fluid through the lumens according to Poiseuille's Law.

In the preferred form of this embodiment, the two larger lumens 72 and 74 are substantially semi-cylindrical with generally D-shaped cross-sections which occupy the substantial majority of the cross sectional area of the body portion 78.

Figure 8:
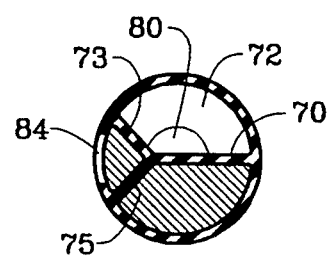
FIG. 8 is an enlarged cross-sectional view of the further alternate embodiment of the present invention of FIG. 6 showing the septum of a triple-lumen catheter constructed in accordance with the present invention taken generally along lines 8—8 of FIG. 6 showing the cross sectional shapes of the venous and third lumens of the present invention.

As shown in FIGS. 7 and 8, the third lumen 76 is located at one diametrical end of the major septum 70, where the septum bifurcates into a pair of generally flat minor septums 73 and 75. Therefore, the third lumen 76 is located between two adjacent corners of the generally D-shaped first and second lumens 72 and 74. As best shown in FIG. 7, the third lumen 76 preferably has a triangularly-shaped cross-section and can be used as needed for the treatment of critically ill patients. Because the third lumen is generally triangular shaped, there is only a slight reduction in the flow capacity of the first and second lumens 72 and 74 and the first and second lumens 72 and 74 are more than capable of supplying a fluid flow rates of 250 ml per minute of blood at a pressure of less than 100 mg of mercury. Additionally, the likelihood of the formation of stagnation zones in the first and second lumens 72 and 74 along the intersection of the minor septums 73 and 75 and the body portion 78 is significantly reduced because the angle of contact between these surfaces is ninety degrees or greater. Because the third lumen is used intermittently and is easier to flush with small amounts of fluid, the presence of potential areas of stagnation is not believed to be as critical as in the high flow and high volume first and second lumens 72 and 74.

Figure 9:
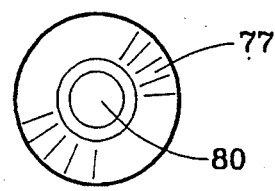
FIG. 9 is an enlarged end view of the further alternate embodiment of the present invention shown in FIG. 6.

At the distal end portion of the catheter of the embodiment shown in FIGS. 6–9, the external surface of the body portion 78 merges into a smoothly tapered frusto-conical tip portion 77. On the inside of the tip portion 77, the blood return lumen or first lumen 72 extends all the way through the tip portion 77 so that it opens into opening or aperture 80. The first lumen 72 bends slightly as it passes through the tip portion 77 so that it opens generally at the center of the distal end of the tip portion 77 as shown in FIG. 9. Within the tip portion 77, the shape of the first lumen gradually changes from the generally D-shaped configuration shown in FIGS. 7 and 8 to the circular cross-section shown in FIG. 9. In addition to the opening 80 at the distal end of the tip portion 77, an auxiliary aperture or opening (not shown) may be preferably formed in the sidewall of the body portion 78 to ensure that the flow of fluid through the first lumen 72 will continue even if the opening 80 is partially or totally blocked.

Figure 10:
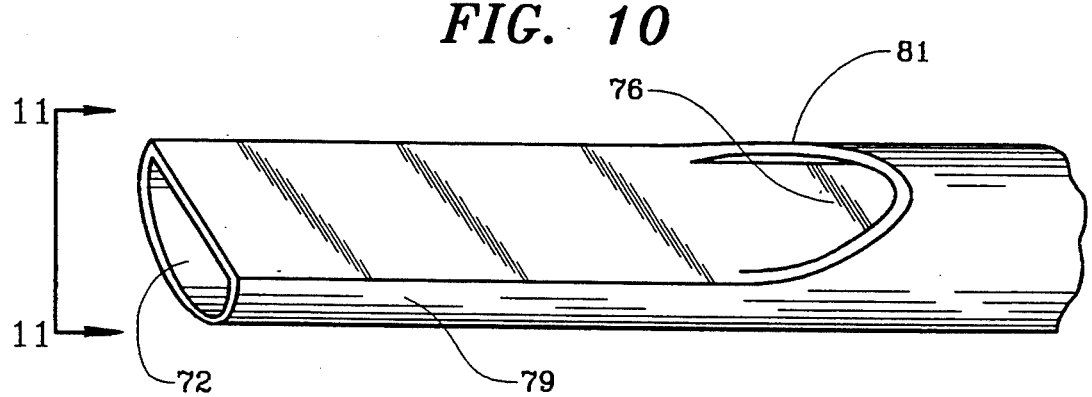
FIG. 10 is an enlarged perspective view of a further alternate embodiment of the present invention generally similar to the embodiment of FIG. 6 showing the distal end portion of an alternate form of the triple-lumen catheter constructed in accordance with the present invention.

As shown in FIGS. 6 and 10, the openings of the first and second lumens 72 and 74 are spaced apart longitudinally along the body portion 78 and tip portion 77 of the catheter. The second lumen 74 terminates at aperture or opening 82 which is spaced apart proximally along the body portion 78 of the catheter from opening 80 to ensure that a venturi effect does not occur during hemodialysis. Additionally, one or more auxiliary apertures or openings (not shown) may be spaced apart along the body portion proximally of opening 82 to permit blood to enter the second lumen in the event that opening 82 is partially or totally blocked during hemodialysis.

The third lumen 76 preferably terminates at aperture or opening 82 which is laterally and rotationally spaced apart from opening 82 along the body portion 78. As shown in FIG. 6, this opening is preferably positioned about midway between openings 80 and 84 and approximately 90 degrees away from opening 84 along the rotational dimension of the body portion 78. Therefore, medications injected into the patient are preferably injected downstream of the intake or second lumen 74 of the catheter such that the medication will not be drawn into the hemodialysis unit. Additionally, blood samples taken through the third lumen 76 will be taken upstream from the return or first lumen 72 of the catheter.

Figure 11:
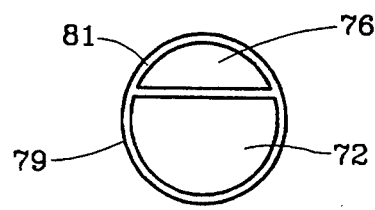
FIG. 11 is an enlarged cross-sectional view of the further alternate embodiment of the present invention of FIG. 10 showing the septum of a triple-lumen catheter constructed in accordance with the present invention taken generally along lines 11—11 of FIG. 10 showing the end of the venous lumen and the end of the third lumen of the present invention.

FIGS. 10 and 11 are illustrative of a different configuration for the tip portion 79 than the tip portion 77 described above and shown in FIG. 6. In this embodiment, the first lumen 72 terminates at the distal end of the tip portion 79 and the third lumen 76 terminates generally at or distally of the intersection of the tip portion 79 and the body portion 78. As shown in FIG. 11, the opening 82 for the third lumen 76 opens along the longitudinal dimension of the body portion 78 and may include tapered side wall members 81 to assist in directing medications from the third lumen downstream into the flow from the first lumen 72.

Figure 12:
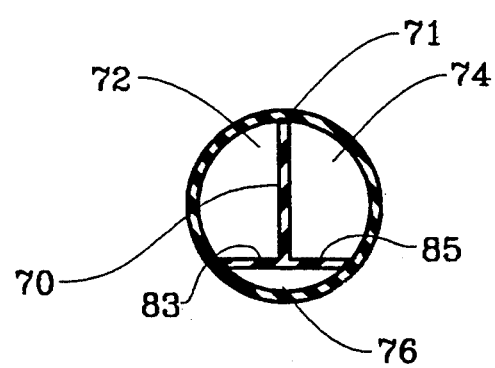
FIG. 12 is an enlarged cross-sectional view of a further alternate embodiment of the present invention showing an alternate septum configuration for a triple lumen catheter.

FIG. 12 illustrates an alternate cross section of the major lumen 70 and the minor lumens 83 and 85 of the catheter of the present invention. In this embodiment, the minor septums 83 and 85 are aligned to form a generally straight line which is preferably perpendicular to the diametrical dimension of the major septum 70. As with the minor septums 73 and 75 described above, the minor septums 83 and 85 of the present embodiment intersect the body portion 78 of the catheter at an angle which is generally equal to or greater than ninety degrees with respect to the body portion to reduce the likelihood of a stagnant zone or area being formed in the first or second lumens 72 and 74.

Figure 13:
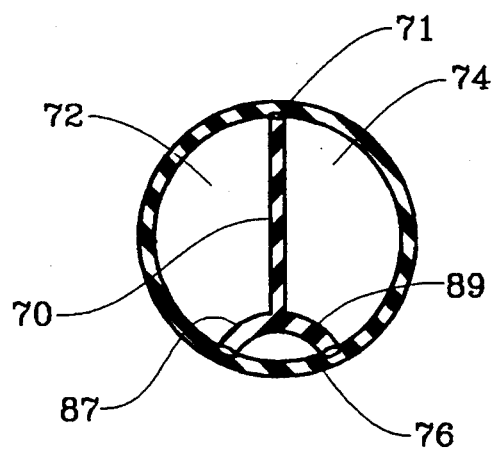
FIG. 13 is an enlarged cross-sectional view of a further alternate embodiment of the present invention showing an alternate septum configuration for a triple lumen catheter.

FIG. 13 is illustrative of an alternate embodiment wherein the minor septums 87 and 89 are curved slightly. As described above with respect to the Mahurkar patent, this configuration is less desirable than the embodiments described above because the flows through the catheter are not optimized. Despite this, it is believed that this configuration will function adequately because the length of the minor septum portions adjacent to the first and second lumens 72 and 74 are only slightly greater than the length of the minor portions disclosed in FIG. 12 and are less than the septum portions disclosed in the Mahurkar patent referred to above.

Figure 14:
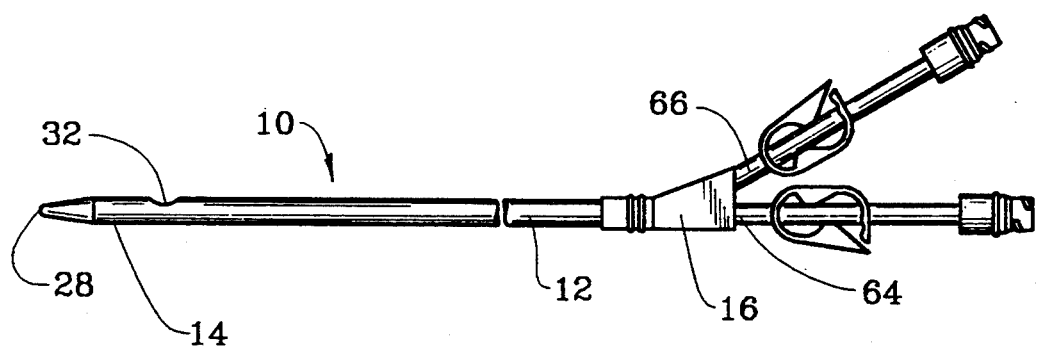
FIG. 14 is an elevated side view of an alternate embodiment of a dual lumen catheter having straight extension members constructed in accordance with the present invention.

As shown in FIG. 14, the embodiment shown in FIGS. 1-4 may also be used on a dual lumen catheter having extension members 64 and 66 which are straight rather than the precurved extension members 18 and 20 shown in FIG. 1. In the present embodiment, the thickness of the inner and/or outer layer of the extension members 64 and 66 may vary along the length of the extension member to facilitate the desired curvature or flexibility of the extension member along the skin of the patient. Additionally, the thickness of the respective layers may be adjusted in the area of the extension member which is normally closed by a clamp to ensure that the sidewalls of the extension member do not stick together to close or restrict the flow of fluid through the extension member after prolonged periods of clamping. The thickness of the respective layers near the clamps may also be varied to ensure that the extension member is not subject to inadvertent tearing after prolonged or repeated use.

Figure 15:
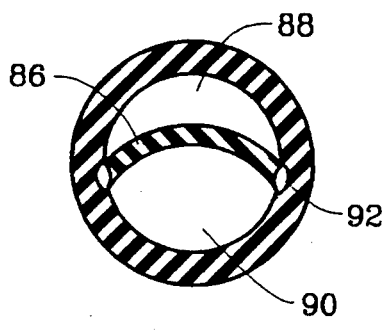
FIGS. 15 and 16 are enlarged cross-sectional views of further alternate embodiments of the present invention.
Figure 16:
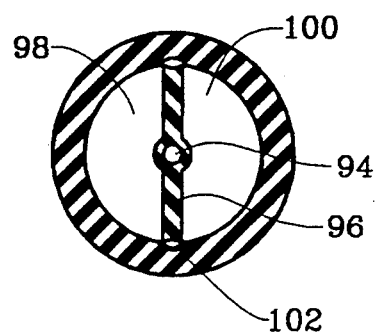

FIGS. 15 and 16 illustrate further embodiments of the present invention. In FIG. 15, the septum 86 is curved slightly and preferably formed of a higher durometer material similar to the material described above with respect to the septum of the preferred embodiment of the present invention. The septum 86 of this embodiment separates the interior of the catheter into two lumens 88 and 90 which preferably function as arterial and venous lumens when the catheter assembly is used for hemodialysis. As described above with respect to FIG. 5, the embodiment shown in FIG. 15 preferably includes an intermediate layer 92 formed at the ends of the septum 86 while the sidewalls of the catheter assembly are preferably formed of a softer, lower durometer material. Alternately, the catheter assembly shown in FIG. 15 may also be formed similar to the preferred embodiment shown in FIG. 3 wherein the higher durometer material surrounds one or both of the lumens 88 and 90.

FIG. 16 illustrates a further variation of the embodiments shown in FIGS. 6-13. In the embodiment shown in FIG. 16, the third lumen 94 is centrally located in the catheter and is preferably formed as part of the septum 96 which separates the remaining two lumens 98 and 100 of the catheter. In this embodiment the septum 96 is preferably formed of a higher durometer material similar to the material described above with respect to the preferred embodiment of the present invention. The intermediate layer 102 is preferably formed at the ends of the septum 96 although it is anticipated that the higher durometer material may be coextruded to surround only the third lumen 94 or all of the lumens of the catheter in a manner similar to the embodiment shown in FIG. 3. Although it is anticipated that the third lumen 94 of the present embodiment will open through the distal end of the catheter tip, the present embodiment may also be formed similar to the embodiment shown in FIG. 14 wherein the third lumen 94 extends through the catheter to an opening located in the sidewall of the catheter assembly.

Although the foregoing is intended to describe the currently preferred forms of the present invention, it is envisioned that a number of variations of the present invention may be considered by a person skilled in the art. Upon reading the foregoing, it is intended that the true scope of the claims of the present invention be determined by the following claims.

What is claimed is:

1. A multiple lumen catheter comprising:
an elongated cylindrical body portion having distal and proximal end portions with one or more internal septums therein to form a plurality of lumens therebetween, and said septums forming at least three longitudinal lumens with the first and second of said lumens having substantially semi-circular transverse cross-sections occupying the major portion of the transverse cross-section of the interior of said body portion and a third lumen having a small transverse cross-section and located at the intersection of the diametral end of the major septum opposite the intersection end of said major septum with said body portion between a pair of linear minor septums which extend linearly between said diametral end of said major septum and said body portion.

2. The catheter of claim 1 wherein said first lumen is formed by said major septum, said body portion and one of said minor septums.

3. The catheter of claim 1 wherein said major septum forms an integral part of said first and second lumens.

4. The catheter of claim 1 wherein said major septum includes a major portion and the transverse width of said major portion of said major septum is flat so that said first and second lumens have generally D-shaped cross-sections.

5. The catheter of claim 1 wherein a major portion of the transverse width of said major septum is flat so that said first and second lumens have substantially similar cross sectional areas.

6. The catheter of claim 1 wherein said third lumen is formed by said minor septums and said body portion so that said third lumen has a generally triangularly shaped cross-section.

7. The catheter of claim 1 wherein said distal end portion of said body portion includes a generally conical tip thereon having a distal end and wherein said conical tip merges smoothly with the outside portion of said body portion and the inside surface of said conical tip merges smoothly with the inside surface of one of said first or second lumens and the distal ends of the other of said lumens being spaced from said distal end of said conical tip.

8. The catheter of claim 7 wherein said other of said lumens are longitudinally spaced from said conical tip and each other.

9. The catheter of claim 7 wherein said first lumen extends all the way through said conical tip and said second lumen terminates at an aperture spaced longitudinally from said distal end of said conical tip and said third lumen terminates at an aperture located longitudinally between said distal end of said conical tip and said aperture of said second lumen.

10. The catheter of claim 1 wherein said minor septums include at least first and second ends and at least one of said first and second ends are integrally connected to an interior surface of said body portion, and said minor septums form said third lumen, and the other of said first and second ends are integral with said major septum.

11. The catheter of claim 1 wherein said minor septums intersect said body portion at an angle of ninety degrees or more along said first and second lumen.

12. A multiple lumen catheter comprising;
an elongate and generally cylindrical body portion,
a septum formed of major and minor septum portions extending across the interior of said body portion and along the length thereof to divide said interior of said body portion into at least three longitudinal lumens,
said major septum extending substantially diametrically across and having one end which intersects said body portion to form first and second lumens which are substantially semi-cylindrical and extend longitudinally on opposite sides thereof,
a plurality of minor septums wherein said minor septums intersect said major septum on the end of said major septum opposite the end of said major septum which intersects said body portion and intersecting said body portion to form a third lumen which is substantially smaller than said first lumen and wherein the angle formed between at least one of said minor septums along said first lumen and said body portion is ninety degrees or greater.

13. The catheter of claim 12 wherein said minor septums are straight and extend between said major septum and said body portion.

14. The catheter of claim 13 wherein said minor septums are generally perpendicular to said major septum.

15. The catheter of claim 14 wherein said first and second lumens are symmetrical.

16. A multiple lumen catheter comprising:
an elongated cylindrical body portion having distal and proximal end portions with one or more internal septums therein to form a plurality of lumens therebetween, and said septums forming at least three longitudinal lumens with the first of said lumens being formed by three corners formed by the intersection of said major septum, said minor septum and said body portion wherein at least two of said corners have an angle of at least ninety degrees with respect to said first lumen and a third lumen having a small transverse cross-section and located at the intersection of the diametral end of the major septum opposite the intersection end of said major septum with said body portion between a pair of linear minor septums which extend between said diametral end of said major septum and said body portion.

17. The catheter of claim 16 wherein said first lumen and said second lumen are symmetrical and substantially semi-circular in cross-section.

18. The catheter of claim 16 wherein said third lumen is formed by the intersection of said minor septums and said body portion and said minor septums are linear between an end of said major septum and said body portion.

19. The catheter of claim 18 wherein said third lumen has a generally triangular cross section.

20. The catheter of claim 16 wherein said first lumen and said second lumen are generally D-shaped and said third lumen opens into and aperture positioned between the apertures of said first lumen and said second lumen.

* * * * *